United States Patent
Cocandeau et al.

(10) Patent No.: US 11,590,070 B2
(45) Date of Patent: Feb. 28, 2023

(54) HYDROALCOHOLIC EXTRACT OF CAMELLIA JAPONICA AND COSMETIC COMPOSITIONS COMPRISING IT

(71) Applicant: CHANEL PARFUMS BEAUTE, Neuilly sur Seine (FR)

(72) Inventors: Vincent Cocandeau, Neuilly sur Seine (FR); Anne Rossignol-Castera, Neuilly sur Seine (FR); Noémie Lemoine, Neuilly sur Seine (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 0 days.

(21) Appl. No.: 17/705,643

(22) Filed: Mar. 28, 2022

(65) Prior Publication Data
US 2022/0313596 A1    Oct. 6, 2022

(30) Foreign Application Priority Data
Mar. 29, 2021    (EP) ..................................... 21305389

(51) Int. Cl.
| | |
|---|---|
| *A61K 36/00* | (2006.01) |
| *A61K 8/9789* | (2017.01) |
| *A61K 8/06* | (2006.01) |
| *A61K 8/92* | (2006.01) |
| *A61Q 19/00* | (2006.01) |

(52) U.S. Cl.
CPC ............ *A61K 8/9789* (2017.08); *A61K 8/062* (2013.01); *A61K 8/922* (2013.01); *A61Q 19/005* (2013.01)

(58) Field of Classification Search
CPC .................................................... A61Q 19/005
See application file for complete search history.

(56) References Cited

FOREIGN PATENT DOCUMENTS

| | | |
|---|---|---|
| JP | 2002-371092 A | 12/2002 |
| JP | 2009155317 A | 7/2009 |
| JP | 2013053108 A | 3/2013 |
| KR | 20070011939 A | 1/2007 |
| WO | 2011/083110 A2 | 7/2011 |
| WO | WO-2011083110 A2 * | 7/2011 ........... A61K 31/728 |
| WO | 2016/016515 A1 | 2/2016 |

OTHER PUBLICATIONS

Nakamura, Melanogenesis inhibitory and fibroblast proliferation accelerating effects of noroleanane—and oleanane-type triterpene oligoglycosides from the flower buds of Camellia japonica. Journal of natural products, (Aug. 24, 2012) vol. 75, No. 8, pp. 1425-1430 (Year: 2012).*
European Search Report and Written Opinion dated Oct. 15, 2021 in corresponding European Application No. 21305389.5; 12 pages.
Karadeniz Fatih et al: "Camellioside A, isolated from Camellia japonica flowers, attenuates UVA-induced production of MMP-1 in HaCaT keratinocytes via suppression of MAPK activation", Experimental and Therapeutic Medicine, vol. 21, No. 1, Nov. 5, 2020 (Nov. 5, 2020), 6 pgs.
Office Action dated Aug. 3, 2022, in corresponding Korean Application No. 10-2022-0037155, 11 pages (with English Translation).
Young Ju Cha et al., "Major Components of Teas Manufactured with Leaf and Flower of Korean Native Camellia Japonica L."; Korean J. Medicinal Crop Sci.; vol. 12; No. 3; Apr. 19, 2004; pp. 183-190 (with English Abstract).
Doosan Encyclopedia; "Camellia Alba Plena"; Sep. 20, 2012; No. 28143; https://www.doopedia.co.kr/photobox/comm/community.do?_method=print&GAL_IDX=120920000843072; 2 pages (with Machine-Generated English Translation).

* cited by examiner

*Primary Examiner* — Qiuwen Mi
(74) *Attorney, Agent, or Firm* — Maier & Maier, PLLC

(57) ABSTRACT

A *Camellia* extract obtained by extracting by ultrasound a powder of *Camellia japonica* flowers, the powder being impregnated with a fatty substance or a mixture of fatty substances, with a hydroalcoholic solvent, and a cosmetic composition including such an extract having in particular a soothing effect for the skin. Also, a non-therapeutic use thereof for soothing the skin.

16 Claims, No Drawings

HYDROALCOHOLIC EXTRACT OF CAMELLIA JAPONICA AND COSMETIC COMPOSITIONS COMPRISING IT

The object of this invention is an extract of the *Camellia japonica* flower, characterized in that it is capable of being obtained by extraction with a hydroalcoholic solvent of *Camellia* flowers pretreated by oil-based extraction, as well as the use of said extract in cosmetics, to soothe and/or reduce inflammation of human skin.

BACKGROUND

The skin is the body's first protective barrier against the environment. It therefore undergoes numerous external assaults which can lead to uncomfortable skin reactions or, in the event of very intense or more serious reactions, to phenomena of irritation and/or inflammation of the skin.

Uncomfortable skin reactions, or alternatively reactions of irritation and/or inflammation of the skin may in particular be induced by contact with chemical products such as cleansers, or may come from mechanical actions such as shaving, exfoliation, peeling, hair removal. They may also be a result of the temperature, climate, ultraviolet radiation, or atmospheric pollution.

There is always a need for new soothing agents in the cosmetic field. There also exists a need for new agents capable of treating and/or reducing skin irritation and/or inflammation reactions in the dermatological field.

SUMMARY

The object of this invention is therefore to propose a novel extract of *Camellia japonica* obtained by means of a specific process, and having soothing and anti-inflammatory cosmetic properties.

The Applicant has already proposed, in its international application WO2011/083110, the implementation of a hydroalcoholic extract of *Camellia*, for effectively combating dryness of the skin. Indeed, in that application, the obtained hydroalcoholic extract of *Camellia* acts by stimulating the expression of HSP32 mRNA, stimulating the expression of the HSP27 protein, and stimulating the expression of the PPAR-β/δ protein on the treated keratinocytes.

However, such an extract does not act on the genes involved in the inflammation-related pathways in normal human keratinocytes, so it does not reduce skin inflammation or act as a soothing agent.

It is thus to the credit of the Applicant to have developed a particular process for preparing a novel hydroalcoholic extract of the *Camellia japonica* flower having soothing properties for the skin which are unknown for extracts of the *Camellia japonica* flower currently on the market, and having an anti-inflammatory action for the skin by inhibiting the expression of genes involved in the inflammation-related pathways in normal human keratinocytes.

An object of the present invention is thus, according to a first aspect, a particular process for preparing a hydroalcoholic extract of *Camellia japonica* flowers, comprising the following steps:
  i. impregnation of a powder of *Camellia* flowers with a fatty substance or a mixture of fatty substances at a temperature above the melting temperature of said fatty substance and under an atmosphere free or essentially free of oxygen, preferably an oil, then separation to obtain an oily extract of *Camellia* flowers and a residual powder of the flowers thus extracted,
  ii. impregnation of the residual powder of flowers that was obtained in step i., by means of an extraction solvent based on a mixture of alcohol and water under an atmosphere free or essentially free of oxygen,
  iii. extraction of said residual powder of flowers by ultrasound, in particular low frequency, and under an atmosphere free or essentially free of oxygen,
  iv. maceration of the solid residue in the extraction solvent and under an atmosphere free or essentially free of oxygen,
  v. clarification, for example by microfiltration, of the hydroalcoholic extract of *Camellia* flowers.

Another object of the invention is, according to a second aspect, a hydroalcoholic extract of *Camellia japonica* flowers, mainly comprising a mixture of sugars, camellioside A, and camellioside B, preferably obtained by means of the process described above.

Another object of the invention is, according to a third aspect, a cosmetic composition comprising at least one such extract of *Camellia japonica* flowers, in a physiologically acceptable medium.

A final object of the invention is, according to a fourth aspect, the non-therapeutic cosmetic use of said extract of *Camellia japonica* flowers, as a soothing and/or anti-inflammatory active ingredient.

DETAILED DESCRIPTION

*Camellia japonica*

*Camellia* is a genus of flowering plants in the Theaceae family, native to eastern and southern Asia from the Himalayan range to Japan and in Indonesia. Among other things, *Camellia* flowers are recognized for their antibacterial, antioxidant, anti-inflammatory, astringent, and tonic properties. The number of species contained in the genus differs depending on the botanist, and varies between 100 and 250 species. Mention may be made in particular of the white-colored flowers, in particular the Alba plena variety, *Camellia japonica* flowers that are very dark red in color of the chocolate red to black red type, in particular the varieties Black magic, Kuro tsubaki, Black domino, Koronkoku, Kon wabisuke, Kuro wabisuke, Murasaki-no-ue, and Sir Victor Davis, and hybrid *Camellia* flowers from Kuro tsubaki whose variety names are Night rider or Black opal. The Black magic and Night rider varieties are the most common varieties of *Camellia japonica* in France. The colors of *Camellia* flowers can vary depending on the pH and the metals and metalloids present in the soil or substrate. Camellias generally bloom from mid-February to April. However, it is possible to obtain flowering as early as October via hormonal treatment.

The extract according to the invention is obtained from *Camellia japonica* flowers, and preferably from white flowers, in particular of the Alba plena variety. Preferably, the *Camellia japonica* flowers used in the invention are grown in France.

The *Camellia japonica* flowers are preferably in the form of a dispersible powder. Dispersible is understood to mean that the *Camellia* flower powder is in a dissociated form capable of being finely dispersed, and for example, the raw material is in particulate form and preferably powdery. Fresh *Camellia* flowers are, for example, first isolated from the stems, then opened and laid flat on drying racks. They are then dehydrated under mild conditions, either at room temperature away from light or in a ventilated dryer at a temperature below 35° C. The flowers are preferably dried until a solids content greater than 80% and preferably greater than 85% is obtained.

The flowers are then reduced to a dispersible powder by any milling process conventionally known to those skilled in the art, for example at room temperature in a cutting mill or, according to a preferred embodiment, by low-temperature milling. For low-temperature milling, the flowers are preferably cooled to −80° C. in a closed, thermostatically-controlled enclosure and immediately milled in a propeller mixer at a temperature between −20 and −80° C. so as to obtain a fine and regular powder. Cryopreservation advantageously makes it possible to ensure effective milling, obtain a homogeneous powder, limit coloration of the powder, and guarantee better preservation of the soothing properties of the molecules contained in the flowers.

Preferably, the dispersible powder of *Camellia japonica* flowers used to prepare the extract according to the invention has a mean particle size of less than 500 µm, preferably less than 300 µm. Powder of *Camellia japonica* flowers has a mild floral odor and a color ranging from creamy white to reddish brown.

Process for Preparing a Hydroalcoholic Extract of *Camellia japonica* Flowers

According to an essential feature of the invention, steps i., ii., iii., and iv. of the process for preparing the *Camellia* extract are carried out in an atmosphere free or essentially free of oxygen. This means working under an inert gas or atmosphere or under vacuum or partial vacuum. The residual oxygen content must be low enough to avoid causing oxidation reactions sensitive to the temperature of the heat treatment. These steps can therefore be carried out under an inert atmosphere, for example under nitrogen and preferably with constant nitrogen sweeping, enabling extraction of the oxygen present or capable of forming. A closed reactor with continuous oxygen extraction via the nitrogen stream may be employed. Nitrogen sparging may also be carried out, associated with the nitrogen stream, at least at the start of the heat treatment. These steps may also be carried out under vacuum. Proceeding in this manner confers an additional advantage, namely the entrainment of volatile materials with a partial deodorizing effect on the mixture.

According to a preferred embodiment, steps i., ii., iii., and/or iv. are conducted in closed reactors in the absence of light or of any oxidizing radiation such as UV.

Step i. Impregnation of *Camellia* Flowers with a Fatty Substance

An object of the invention is a process for preparing a hydroalcoholic extract of *Camellia* flowers, comprising a first step i. of impregnation of a powder of *Camellia* flowers with a fatty substance or a mixture of fatty substances at a temperature above the melting point of said fatty substance and under an atmosphere free or essentially free of oxygen, preferably an oil, then separation to obtain an oily extract of *Camellia* flowers and the solid residue from the flowers thus extracted.

A process allowing the preparation of an oily extract of *Camellia*, leading to obtaining a residual powder of *Camellia* flowers (co-product) is for example described in detail in application WO 2016/016515.

In particular, the fatty substance used as the extraction solvent is preferentially of plant origin, and may be a plant oil which is liquid at room temperature (20-25° C.), a plant butter having a melting point between 25 and 40° C., or a plant wax having a melting point above 40° C. According to a preferred embodiment, the fatty substance used as the extraction solvent is a plant oil that is liquid at a temperature below room temperature, and in particular liquid at a temperature of approximately 20° C.

As examples of oils that can be used to obtain the extract according to the invention, mention may be made of *Camellia* oil, rapeseed oil, sunflower oil, olive oil, sesame oil, apricot kernel oil, grapeseed oil, sweet almond oil, safflower oil, hazelnut oil, argan oil, muscat rose oil, evening primrose oil, borage oil, liquid jojoba wax, and mixtures thereof. Preferably, an oil that is a source of omega-6 polyunsaturated fatty acids which can play a positive role in membrane fluidity and skin hydration will be chosen.

Step i. is carried out at a temperature greater than or equal to the melting point of the fatty substance or mixture of fatty substances used. In particular, the temperature is advantageously between this melting temperature and the melting temperature +20° C., preferably +10° C. Room temperature (20-25° C.) is perfectly suitable for fatty substances such as oils that are liquid at this temperature. The duration of step i. may be between 1 and 48 hours, preferably between 5 and 40 hours, more preferably between 12 and 36 hours, even more preferably between 20 and 30 hours, and according to a particularly preferred embodiment, the duration of the impregnation step i. is approximately 24 hours.

Step i. is carried out under an atmosphere free or essentially free of oxygen, and preferably under an atmosphere saturated with nitrogen.

The process enabling the impregnation of the *Camellia* flower powder with a fatty substance may also comprise a step i.2. of micro-dispersion of the *Camellia* flower powder in the fatty substance at a temperature above the melting temperature of said substance, in an atmosphere free or essentially free of oxygen.

This step i.2. may be carried out by treating the mixture by ultrasonic cavitation. Cavitation and dispersion under ultrasonic waves are preferably carried out in a closed reactor equipped with a low-frequency ultrasound generator for the cavitation, in particular less than 100 kHz and preferably approximately 20 to 30 kHz.

The duration of the ultrasound treatment in step i.2. is in particular between 2 and 30 minutes, preferably between 10 and 20 minutes.

Step i.2. is advantageously carried out at room temperature or at a temperature above the melting point of the fatty substance or fatty substances used. The temperature is advantageously between this melting temperature and the melting temperature +20° C., preferably +10° C. Room temperature (20-25° C.) is ideal for oils that are liquid at this temperature.

The process for obtaining the *Camellia* flower extract according to the invention may also comprise a step i.3. of heating the mixture obtained in step i. or i.2. of said *Camellia* flower powder with said fatty substance or substances, at a temperature between 80 and 180° C. for a period of between 1 and 10 minutes, under an atmosphere free or essentially free of oxygen.

In a preferred embodiment, the temperature of step i.3. is between 80 and 150° C., preferably between 90 and 130° C.

The heating step i.3. is carried out for a very short duration ranging from 1 to 10 minutes, preferably from 1 to 5 minutes, and more preferably from 1 to 3 minutes, this duration corresponding to the time the treatment temperature is maintained once this temperature is reached. The temperature rise time is also very short, in particular less than or equal to 5 minutes, preferably from 1 to 5 min, and more preferably from 1 to 3 minutes.

Any system for rapid thermal heating may be used, and in a preferred embodiment, the thermal treatment is done via microwaves. The use of a microwave source within a closed reactor makes it possible to reach the desired temperatures in a very short time. High-temperature heating also makes it possible to increase the capacity for solubilization of the fatty substance used and promotes contact between the *Camellia* flower powder and said fatty substance, thus boosting the extraction yield. According to a preferred embodiment, the microwave generator used for heating in step i.3. has a power output ranging from 500 to 10000 Watts per kilogram of mixture, preferably approximately 700 to 1500 Watts per kilogram of mixture, and more preferably approximately 1000 Watts per kilogram of mixture.

According to one particular embodiment, an oxygen scavenger or reducer compound is added during step i.3. or just before. It is thus possible to add vitamin C in the form of pure ascorbic acid, salt such as sodium ascorbate or ascorbyl palmitate, citric acid or lactic acid in free form or ester, or lecithins, or a combination of these compounds. An individual quantity of 0.01 to 1% by weight will be added to the mixture, preferably 0.1 to 0.5% by weight to the mixture.

Steps i., i.2., and/or i.3. are advantageously carried out in the absence of light or of any oxidizing radiation such as UV, to limit the risk of photo-oxidation and degradation of photosensitive molecules.

Steps i., i.2., and/or i.3. may be carried out in a closed reactor with or without stirring of the mixture and preferably with stirring.

According to one embodiment, the process consists of a combined sequence of steps i., i.2., and/or i.3., the order of steps i.2. and i.3 being immaterial, each step being carried out at least once each.

To finish step i., one or more step(s) i.4. of separation of the oily extract and the residual powder of *Camellia japonica* flowers are implemented. These separation methods may for example be selected among filtration, decantation, centrifugation, spin-drying, or a combination of these techniques. Preferably, the separation is carried out by centrifugation or filtration. This separation step may be carried out at a temperature between 40 and 60° C. in a centrifugal separator fitted with a filter cloth having a porosity of less than 10 µm and preferably less than or equal to 5 µm and at a speed of between 500 and 2500 rpm and preferably between 1000 and 1500 rpm.

The separation step or steps make it possible to separate the oily extract from the residual powder of *Camellia japonica* flowers and simultaneously to obtain an oily extract that is clear to the eye and free of microparticles in suspension.

At the end of steps i., i.2., i.3., and/or i.4., one obtains an oily extract of *Camellia* flowers and a residual powder of *Camellia* flowers having therefore previously undergone an oil-based extraction.

This residual powder of flowers used in the process according to the invention is in the form of a fatty plant-based cake, or a filter cake, brown-colored and of homogeneous appearance, easily dispersible in a liquid.

Step ii. Impregnation of the Residual Powder of *Camellia* Flowers

At the end of step i., the process according to the invention implements a step ii. of impregnation of the residual powder of flowers obtained in step i. (cake) by means of an extraction solvent based on a mixture of alcohol and water, under an atmosphere free or essentially free of oxygen.

The impregnation of the residual powder of *Camellia* flowers may be carried out by alcohol extraction using at least one monoalcohol such as ethanol, methanol, or iso-propanol, and/or at least one glycol such as propylene glycol (propanediol) or dipropylene glycol, mixed with water.

The extraction is carried out in the absence of any solvent other than water and the alcohols.

The solvent used in step ii. is preferably a mixture of polyol and water, and more preferably of propanediol and water.

According to a preferred embodiment, the ratio of the volume of alcohol:water of the extraction solvent used in step ii. is between 95%/5% and 50%/50%, preferably between 90%/10% and 70%/30%, and more preferably between 85%/15% and 75%/25%.

The impregnation is generally carried out by dispersing or gently stirring the residual powder of *Camellia* flowers in one or more of the solvents mentioned above, at room temperature, i.e. between 20 and 25° C., for a period of approximately 15 minutes to 2 hours and preferably from 30 minutes to 1 hour.

The ratio of solvent/material (by volume/weight) may for example be between 1:1 and 20:1 and preferably between 5:1 and 10:1.

This dispersion and mixing step is common in the field of plant extracts, and the person skilled in the art is able to adjust the parameters and choose the stirring and dispersion tools on the basis of his general knowledge.

Step iii. Ultrasound-Assisted Extraction of Residual Powder of Flowers

The process according to the invention then implements a step of extracting the residual powder of flowers by ultrasonic cavitation and under an atmosphere free or essentially free of oxygen.

This step iii. not only allows homogeneous microdispersion of the residual powder of *Camellia* flowers in the extraction solvent, but also allows rupturing the plant cells of said flowers which releases the molecules contained in these cells . . . . Cavitation and dispersion under ultrasonic waves are preferably carried out in a closed reactor equipped with a low-frequency ultrasound generator for the cavitation, in particular less than 100 kHz and preferably approximately 20 to 30 kHz.

The duration of the ultrasound treatment is in particular between 15 and 60 minutes, preferably between 30 and 40 minutes.

Step iii. is advantageously carried out at room temperature (between 20 and 25° C.) and under an atmosphere free or essentially free of oxygen.

Step iv. Maceration of the Residual Powder of *Camellia* Flowers

Once the ultrasound-assisted extraction has been carried out, the process according to the invention implements a step iv. of maceration of the residual powder of flowers in the extraction solvent, which allows the extracted molecules to diffuse into the hydroalcoholic solvent.

This step consists of leaving the mixture of flower powder and extraction solvent to stand for a period of between 30 min and 3 hours and preferably between 1 hour and 2 hours.

Step iv. is advantageously carried out at room temperature (between 20 and 25° C.) and under an atmosphere free or essentially free of oxygen.

Step v. Clarification of the Hydroalcoholic Extract

To finish, the process according to the invention comprises one or more step(s) of clarification of the hydroalcoholic extract.

Clarification is understood to mean all mechanical separations known to those skilled in the art.

They may for example be selected among filtration, decantation, centrifugation, spin-drying, or a combination of these techniques.

Preferably, the separation is carried out by filtration, more preferably by microfiltration in two stages:
- a first centrifugal microfiltration called spinning, on a filter cloth having a porosity of less than 5 microns and preferably less than or equal to 1 micron, then
- a second clarifying microfiltration on a filtration plate having a porosity of less than 1 micron and preferably less than or equal to 0.2 micron.

Centrifugal microfiltration is understood to mean the simultaneous use of centrifugation and filtration. The mixture is placed in a stainless steel bowl fitted with a filter cloth which the liquid phase passes through and is thus clarified while the solid phase remains inside the basket. This operation may be carried out at a temperature of between 20 and 25° C. in a centrifugal separator fitted with a filter cloth having a porosity of less than 5 μm and preferably less than or equal to 1 μm and at a speed of between 500 and 2500 rpm and preferably between 1000 and 1500 rpm.

Clarifying microfiltration is understood to mean the use of a plate made of inert material having a porosity of less than or equal to 1 micron, to ensure the separation of very fine particles present in suspension in a liquid. If the porosity of the plate is 0.2 microns or less, then the filtration also eliminates the microorganisms present in the liquid and the filtration is said to be sterilizing. This operation may be carried out at a temperature between 20 and 25° C. on a plate filter fitted with a filtration plate having a porosity of 0.2 μm. The liquid may be advanced by a pump or by the production of positive pressure through nitrogen.

The clarification steps make it possible to obtain a hydroalcoholic extract that is both substantially clear to the eye and free of suspended microparticles.

Hydroalcoholic Extract of *Camellia japonica* Flowers

The invention that is the object of this application also covers a hydroalcoholic extract of *Camellia* flowers, mainly comprising a mixture of sugars, camellioside A, and camellioside B:

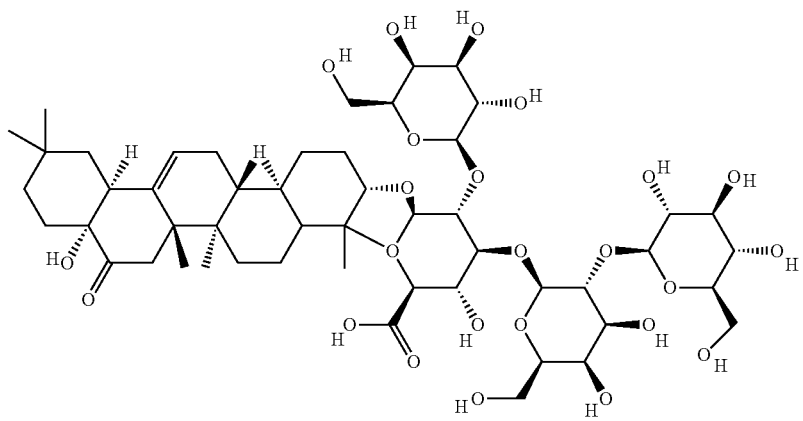

Camellioside A

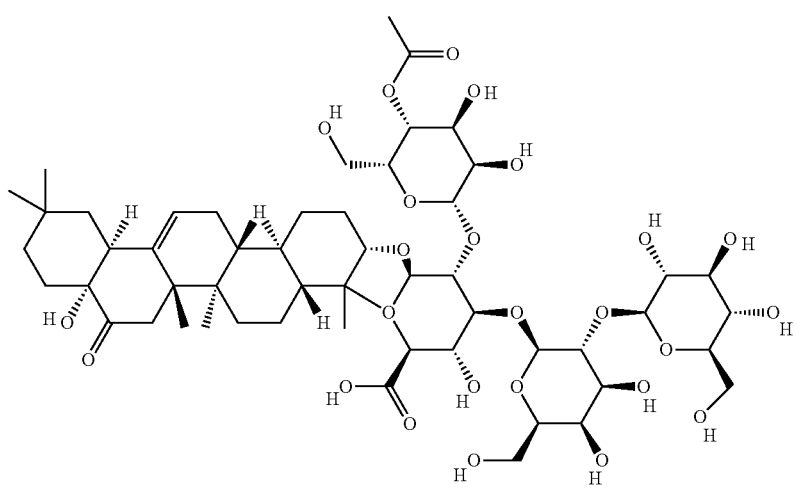

Camellioside B

The sugars present in the extract are preferably selected among glucose, fructose, and a mixture thereof, and preferably a mixture of glucose and fructose.

The hydroalcoholic extract of *Camellia japonica* flowers which is the object of this invention comprises sugars and camelliosides in a mass proportion of approximately 2:1 in the extract.

The hydroalcoholic extract of *Camellia japonica* flowers which is the object of this invention may in particular be obtained by means of the process described above.

The extract of *Camellia japonica* flowers is used according to the invention for non-therapeutic cosmetic purposes, for a soothing and/or anti-inflammatory effect on the skin.

The soothing and/or anti-inflammatory effect of the extract according to the invention may be observed in particular by a reduction in the expression of the genes involved in inflammation-related pathways in normal human keratinocytes, according to the usual techniques well-known to those skilled in the art.

The genes involved in inflammation-related pathways in normal human keratinocytes include B2M (beta-2-microglobulin), HLA-B (major histocompatibility complex, class I, B), IL1A (interleukin 1 alpha), SERPINE1 (serpin family E member 1), ACVR1B (activin A receptor type 1B), CEBPB (CCAAT enhancer binding protein beta), TNF (tumor necrosis factor), and HLA-DQB1 (major histocompatibility complex, class II, DQ beta 1).

Cosmetic Composition

A further object of this invention is a cosmetic composition comprising, in a physiologically acceptable medium, at least one *Camellia japonica* flower extract.

Preferably, the composition according to the invention, containing the *Camellia japonica* flower extract, is applied to irritated, preferably non-pathological skin. It can advantageously be applied to the skin of the face, neck, hands, and possibly the upper chest, or alternatively to any part of the body. The composition containing this extract may be applied in the morning and/or evening, to the whole of the face, neck, hands, and possibly the upper chest, or even the body.

The composition used according to the invention generally comprises, in addition to the extract described above, a physiologically acceptable and preferably cosmetically acceptable medium, meaning one which is suitable for use in contact with human skin with no risk of toxicity, incompatibility, instability, or allergic response, and in particular which does not cause sensations of discomfort (redness, tightness, tingling).

Advantageously, said cosmetic or dermatological composition may be in the form of a powder, emulsion, microemulsion, nanoemulsion, suspension, solution, lotion, cream, aqueous or hydroalcoholic gel, foam, serum, solution or dispersion for aerosol, or dispersion of lipid vesicles.

In the case of an emulsion, it may be a water-in-oil or oil-in-water emulsion.

The cosmetic or dermatological composition according to the invention may also comprise a solvent chosen according to the various ingredients and the form of administration.

Examples include water (preferably demineralized water or floral waters), or an alcohol such as ethanol.

Said cosmetic composition may also comprise, in addition to the extract according to the invention:

at least one additive that is common in the field, for example such as at least one compound chosen among an emollient or humectant, a gelling and/or thickening agent, a surfactant, an oil, an active agent, a coloring agent, a preservative, an antioxidant, an active agent, an organic or inorganic powder, a sunscreen, and a fragrance.

one or more humectant(s), such as polyols (glycerine, diglycerine, propanediol, caprylyl glycol, pentylene glycol, hexanediol), sugars, glycosaminoglycans such as hyaluronic acid and its salts and esters, and polyquaterniums such as Lipidure-PMB. Said humectant will be present in the composition at a content of approximately 0 to 30%, preferably 0.005 to 10% by total weight of the composition.

one or more emollient agent (s) which may be chosen, for example, among esters such as jojoba esters, esters of fatty acids and of fatty alcohol (octyldodecyl myristate, triethylhexanoin, dicaprylyl carbonate, isostearyl isostearate, caprylic/capric triglyceride), butters such as shea butters (butyrospernum parkii butter extract, shea butter ethyl esters, marketed under the names LIPEX SHEASOFT, LIPEX SHEA-U, LIPEX SHEA, LIPEX SHEALIGHT, LIPEX SHEA TRIS) or moringa butter (moringa oil/hydrogenated moringa oil esters), waxes (*acacia decurrens* flower wax & *helianthus annuus* seed cera seed wax, C10-18 triglycerides), plant oils, phytosqualane, alkanes (undecane, tridecane). Said emollient agent will be present in the composition at a content of approximately 0.1 to 30%, preferably 0.5 to 10% by total weight of the composition.

one or more gelling and or thickening agent(s) for the aqueous phase, chosen for example among cellulose derivatives, gums of plant origin (guar, carob, alginates, carrageenans, pectins), of microbial origin (xanthan), clays (laponite), crosslinked or non-crosslinked hydrophilic or amphiphilic homo- and copolymers of acryloyl-methylpropane sulfonic acid (AMPS) and/or acrylamide and/or acrylic acid and/or salts or esters of acrylic acid (marketed under the names ARISTOFLEX AVC, Aristoflex AVS, Aristoflex HMB, SIMULGEL NS, Simulgel EG, Simulgel 600, Simulgel 800, Pemulen, carbopol, Sepiplus 400, Seppimax zen, Sepiplus S, COSMEDIA SP). Said gelling and/or thickening agent will be present in the composition at a content of approximately 0.1 to 10% by total weight of the composition.

one or more surfactant(s), such as lecithins, polyglycerol derivatives, sugar derivatives (derivatives of glucosides or xylosides marketed under the name MONTANOV 68, MONTANOV 202, Montanov 82, MONTANOV L, EASYNOV), phosphates (C20-22 alkyl phosphate marketed under the name SENSANOV WR). Said surfactant will be present at a content of approximately 0.1 to 8%, preferably 0.5 to 3% by weight, relative to the total weight of the composition.

one or more active agent(s) of natural, biotechnological, or synthetic origin, having biological activity and having an effectiveness on the skin via biological sites, for example chosen among vitamins such as vitamin C and its derivatives (ascorbyl glucoside, 3-O-ethyl ascorbic acid, ascorbyl tetraisopalmitate), vitamin A and its derivatives, vitamin E and its derivatives, vitamin B3 or Niacinamide, panthenol, trace elements, allantoin, adenosine, peptides (Palmitoyl tetrapeptide-7, Palmitoyl Tripeptide-1, Palmitoyl Pentapeptide-4, Acetyl Dipeptide-1 Cetyl Ester, Acetyl Tetrapeptide-5 marketed under the name NP RIGIN, MATRIXYL 3000, IDEALIFT, EYESERYL), plant extracts (*Glycyrrhiza glabra* extract, *Centella asiatica* leaf extract, *Secale cereale* seed extract), yeast extracts, alpha hydroxy acids such as glycolic or lactic acid, tranexamic acid and its derivatives such as cetyl tranexamic ester etc. Said active agent will be present in the composition at a content of approximately 0.1 to 10% by total weight of the composition.

Other additives usually used in cosmetics may also be present in the composition according to the invention, in particular preservatives, antioxidants, or fragrances well known in the technical field.

The person skilled in the art is able to choose, among all of these possible additives, both the type and the amount of additives to be added to the composition such that the composition retains all of its properties.

Another object of the invention is the cosmetic use of the *Camellia japonica* flower extract as described above or of the cosmetic composition described above for soothing and/or reducing inflammation in human skin.

In this embodiment, the extract or composition is applied to non-pathological irritated skin.

The invention will now be illustrated by the following non-limiting examples.

Example 1: Preparation of a Hydroalcoholic Extract of *Camellia japonica* Alba Plena in Accordance with the Invention Step i.

We first carried out the oil-based extraction of *Camellia* flowers under the conditions described in example 1 of application WO2010112760.

Step ii.

The residual powder of flowers obtained at the end of step i. is mixed in a mass proportion of 1:8 into a mixture consisting of 80% propanediol and 20% analytical-grade water. The mixing is carried out in a stainless steel reactor equipped with a propeller agitator. The powder is dispersed in the extraction mixture at room temperature for 45 min in the closed reactor while stirring and under a nitrogen stream.

Step iii.

The mixture is then subjected to ultrasonic cavitation at 25 kHz for 30 min in a closed reactor under a nitrogen stream.

Step iv.

The mixture is then left in the closed reactor under a nitrogen stream without stirring for 2 hours at room temperature.

Step v.

After the maceration step iv., the mixture is spun on a filter cloth with a porosity of 1 micron. The hydroalcoholic extract is then filtered through a plate filter equipped with plates with a porosity of 0.2 microns. The spinning and plate microfiltration are carried out at room temperature.

The final hydroalcoholic extract is clear, fluid, homogeneous, orange-yellow in color, and has a flowery fragrance. It should be kept cold until use.

Example 2: Inhibition of Inflammation-Related Pathways in Normal Human Keratinocytes Treated with the *Camellia* Extract Obtained in Example 1

Protocol: Normal human epidermal keratinocytes from three different donors were seeded in a 24-well plate and cultured in keratinocyte-SFM (k-SFM) supplemented medium for 48 h at 37° C. and 5% $CO_2$. The cells were then incubated with or without (untreated condition) 0.1% of the *Camellia* extract prepared in Example 1, for 48 hours. Each condition was carried out in duplicate. Total RNAs were extracted using TriPure Isolation Reagent® according to the protocol recommended by the supplier. The complementary DNAs were synthesized and a transcriptome was constructed on the Affymetrix GeneChip Human Transcriptome Array 2.0 chip. Bioinformatics analysis of the genes whose expression is modulated at least by a factor of 2 was carried out with the Ingenuity Pathway Analysis software (IPA®, QIAGEN). This software collects information about molecule-to-molecule interactions, biological networks, and canonical pathways in the Ingenuity Knowledge database.

Results: The cellular functions significantly inhibited by the hydroalcoholic *Camellia* extract according to the invention are mainly pathways involved in the inflammatory immune response. The genes involved in these various pathways as well as their level of inhibition by the hydroalcoholic *Camellia* extract according to the invention versus the untreated control (level of expression >2) are reported in Table I.

TABLE I

List of genes involved in the inflammation-related pathways whose expression is reduced by the hydroalcoholic *Camellia* extract according to the invention.

| Symbol | Name of gene | Level of expression (vs untreated control) |
|---|---|---|
| B2M | beta-2-microglobulin | −10,500 |
| HLA-B | major histocompatibility complex, class I, B | −10,150 |
| IL1A | interleukin 1 alpha | −2,580 |
| SERPINE1 | serpin family E member 1 | −2,800 |
| ACVR1B | activin A receptor type 1B | −2,690 |
| CEBPB | CCAAT enhancer binding protein beta | −2,380 |
| TNF | tumor necrosis factor | −2,120 |
| HLA-DQB1 | major histocompatibility complex, class II, DQ beta 1 | −2,190 |

The analyses were performed in IPA with a cutoff of 2: all targets with a level of expression <−2 or >2 are taken into account in the analysis and considered to be significantly modulated effectively.

HLA-B is part of the major histocompatibility complex and B2M is known to be associated with this complex which it also contributes to regulating.

Keratinocytes contribute to initiating the inflammatory response via the secretion of pro-inflammatory cytokines such as TNF-α and IL-1α. They also play a role in skin immunity. Indeed, they express major histocompatibility molecules (B2M, HLA-B, HLA-DQB1, etc.) involved in presenting antigens to effector immune cells. On the other hand, with age and the various stresses to which skin is subjected, some cells become capable of secreting stress messengers (e.g. pro-inflammatory interleukin IL-1α, plasminogen activator inhibitor-1 (PAI-1) encoded by the gene SERPINE1, CEPBβ . . . ) generating an inflammatory skin environment.

By its ability to inhibit the expression of various genes involved in skin inflammation, the hydroalcoholic extract of white *Camellia* according to the invention has a soothing cosmetic potential.

Example 3: Cosmetic Composition

The following compositions can be prepared in a conventional manner for those skilled in the art. The quantities indicated below are expressed in percentages by weight. The ingredients are identified by their INCI name.

A—Oil/Water Gel Emulsion

| INCI name | (% W/W) |
|---|---|
| *Limnanthes alba* (meadowfoam) seed oil | 1-10 |
| Butyrospermum parkii butter (LIPEX SHEASOFT) | 1-10 |
| Butyrospermum parkii butter extract (LIPEX SHEA TRIS) | 1-10 |
| *Camellia oleifera* seed oil | 1-10 |
| Cetyl ethylhexanoate | 1-5 |
| Squalane | |
| Ammonium acryloyldimethyltaurate/VP copolymer | 0.1-5 |
| ACRYLATES/C10-30 ALKYL ACRYLATE CROSSPOLYMER | 0.1-2 |
| Xanthan gum | 0.01-5 |
| *ORYZA SATIVA* (RICE) POWDER | 0.1-5 |
| Sodium hyaluronate | 0.01-3 |
| Glycerin | 1-30 |
| Polyquaternium-51 | 1-10 |
| Adenosine | 0.1-0.5 |
| Niacinamide | 0.1-5 |
| Palmitoyl Tetrapeptide-7 | 1-5 |
| *Secale cereale* (rye) seed extract | 0.1-5 |
| Tocopheryl acetate | 0.1-5 |
| Hydroalcoholic extract of *Camellia japonica* flowers according to the invention | 0.001-10 |
| Yeast extract | 0.1-5 |
| Glycyrrhiza Glabra extract | 0.1-5 |
| Glycols (Caprylyl Glycol and/or Pentylene Glycol and/or Butylene Glycol and/or propanediol) | 0.1-10 |
| Water | QS 100 |

B—Oil/Water Cream Emulsion

| INCI name | (% w/w) |
|---|---|
| Jojoba esters | 1-5 |
| *Limnanthes alba* (meadowfoam) seed oil | 0.1-5 |
| C8-12 ACID TRIGLYCERIDE | 1-5 |
| Lauroyl lysine | 1-5 |
| *Camellia oleifera* seed oil | 1-10 |
| Phytosteryl/octyldodecyl lauroyl glutamate | 1-5 |
| Squalane | 1-10 |
| Ammonium acryloyldimethyltaurate/VP copolymer | 1-5 |
| Polyglyceryl-6 distearate & jojoba esters & polyglyceryl-3 beeswax & cetyl alcohol | 1-7 |
| Xanthan Gum | 0.01-2 |
| Centella asiatica leaf extract | 0.1-5 |
| Adenosine | 0.1-0.5 |
| Niacinamide | 0.1-5 |
| *Secale cereale* (rye) seed extract | 0.1-5 |
| Palmitoyl tripeptide-1 & palmitoyl tetrapeptide-7 | 1-5 |
| Tranexamic acid cetyl ester | 0.001-5 |
| Ascorbyl glucoside | 0.001-5 |
| Yeast extract | 1-3 |
| Saccharide isomerate | 1-5 |
| Hydroalcoholic extract of *Camellia japonica* flowers according to the inventions | 0.001-10 |
| Glycyrrhiza Glabra extract | 0.001-5 |
| Water | QS 100 |

These compositions can be applied to the skin every day, morning and/or evening.

The invention claimed is:

1. A hydroalcoholic extract of *Camellia japonica* flowers, mainly comprising a mixture of sugars, camellioside A, and camellioside B.

2. The hydroalcoholic extract according to claim 1, wherein the sugars and the camelliosides are present in the extract in a mass proportion of approximately 2:1.

3. The hydroalcoholic extract according to claim 1, wherein it is obtained by means of a process comprising the following steps:

i. impregnation of a powder of *Camellia* flowers with a fatty substance or a mixture of fatty substances at a temperature above the melting temperature of said fatty substance and under an atmosphere free or essentially free of oxygen, then separation to obtain an oily extract of *Camellia* flowers and a residual powder of the flowers thus extracted, ii. impregnation of the residual powder of flowers that is obtained in step i., by means of an extraction solvent based on a mixture of alcohol and water under an atmosphere free or essentially free of oxygen, iii. extraction of said residual powder of flowers by ultrasound and under an atmosphere free or essentially free of oxygen, iv. maceration of said powder in the extraction solvent and under an atmosphere free or essentially free of oxygen, and v. clarification of the hydroalcoholic extract of *Camellia* flowers.

4. The hydroalcoholic extract according to claim 2, wherein the *Camellia* flower comes from variety *Camellia japonica alba plena*.

5. A cosmetic composition comprising at least one extract of *Camellia japonica* flowers according to claim 1, in a physiologically acceptable medium.

6. A non-therapeutic cosmetic method of soothing human skin, comprising applying to the human skin in need thereof an effective amount of an extract of *Camellia japonica* flowers according to claim 1, as a soothing active ingredient.

7. A process for preparing a hydroalcoholic extract of *Camellia japonica* flowers, comprising the following steps:

i. impregnation of a powder of *Camellia* flowers with a fatty substance or a mixture of fatty substances at a temperature above the melting temperature of said fatty substance and under an atmosphere free or essentially free of oxygen, then separation to obtain an oily extract of *Camellia* flowers and a residual powder of the flowers thus extracted, ii. impregnation of the residual powder of flowers that is obtained in step i., by means of an extraction solvent based on a mixture of alcohol and water under an atmosphere free or essentially free of oxygen, iii. extraction of said residual powder of flowers by ultrasound and under an atmosphere free or essentially free of oxygen, iv. maceration of said powder in the extraction solvent and under an atmosphere free or essentially free of oxygen, v. clarification of the hydroalcoholic extract of *Camellia* flowers.

8. The process according to claim 7, wherein steps i., ii., iii., and iv. are carried out under a nitrogen atmosphere.

9. The process according to claim 7, wherein the powder of *Camellia japonica* flowers is in the form of a dispersible product obtained by milling at a temperature between −20 and −80° C.

10. The process according to claim 7, wherein the powder of *Camellia* flowers comes from variety *Camellia japonica alba plena*.

11. The process according to claim 7, wherein the fatty substance or substances used in step i. is a plant oil which is liquid at room temperature, a plant butter having a melting point between 25 and 40° C., or a plant wax having a melting point above 40° C., and the fatty substance(s) is an oil selected among camellia oil, rapeseed oil, sunflower oil, olive oil, sesame oil, apricot kernel oil, grapeseed oil, sweet almond oil, safflower oil, hazelnut oil, argan oil, muscat rose oil, evening primrose oil, borage oil, liquid jojoba wax, and mixtures thereof.

12. The process according to claim 7, wherein the extraction solvent used in step ii. is a mixture of polyol and water.

13. The process according to claim 12, wherein the ratio of the volume of polyol: water of the extraction solvent used in step ii. is between 95/5 and 50/50.

14. The process according to claim 13, wherein step iii. of ultrasound-assisted extraction is carried out for a duration of between 15 and 60 minutes, at a cavitation frequency of less than 100 kHz.

15. The process according to claim 14, wherein the clarification step v. is carried out by filtration, in two stages:
- a first centrifugal microfiltration on a filter cloth having a porosity of less than 5 microns, then
- a second clarifying microfiltration on a filtration plate having a porosity of less than 1 micron.

16. The process according to claim 7, wherein steps i., ii., iii., and/or iv. are conducted in the absence of light or of any oxidizing radiation.

\* \* \* \* \*